United States Patent
Tustin et al.

(10) Patent No.: US 10,240,083 B2
(45) Date of Patent: Mar. 26, 2019

(54) THICKENING OF FLUIDS

(71) Applicants: Gary John Tustin, Sawston (GB); Valerie Lafitte, Stafford, TX (US); Bruno Drochon, Houston, TX (US)

(72) Inventors: Gary John Tustin, Sawston (GB); Valerie Lafitte, Stafford, TX (US); Bruno Drochon, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 124 days.

(21) Appl. No.: 14/397,647

(22) PCT Filed: May 10, 2013

(86) PCT No.: PCT/IB2013/053805
§ 371 (c)(1),
(2) Date: Oct. 29, 2014

(87) PCT Pub. No.: WO2013/168136
PCT Pub. Date: Nov. 14, 2013

(65) Prior Publication Data
US 2015/0129226 A1    May 14, 2015

Related U.S. Application Data

(60) Provisional application No. 61/646,019, filed on May 11, 2012.

(51) Int. Cl.
*C09K 8/88* (2006.01)
*E21B 43/16* (2006.01)
(Continued)

(52) U.S. Cl.
CPC .............. *C09K 8/887* (2013.01); *A61K 8/737* (2013.01); *A61K 8/8117* (2013.01);
(Continued)

(58) Field of Classification Search
None
See application file for complete search history.

(56) References Cited

U.S. PATENT DOCUMENTS 5,478,575 A * 12/1995 Miyazaki ............. A61K 9/0019
424/487
5,981,446 A    11/1999 Qiu et al.
(Continued)

FOREIGN PATENT DOCUMENTS

WO    2008/096288    8/2008
WO    2010/105070    9/2010

OTHER PUBLICATIONS

A. Kikuchi et al., Glucose-Sensing Electrode Coated with Polymer Complex Gel Containing Phenyl-boronic Acid, Anal. Chem., vol. 68, pp. 823-828, 1996.*
(Continued)

*Primary Examiner* — Jeffrey D Washville

(57) ABSTRACT

An aqueous fluid, possibly a wellbore fracturing fluid, comprises an aqueous solution or dispersion of a first polymer, which may be polysaccharide, as a thickener and a cross linking agent to enhance the viscosity of the fluid by crosslinking the first polymer, wherein the crosslinking agent is a second polymer comprising at least one polymer chain with phenyl boronate groups distributed along the polymer chain and the phenyl boronic acid groups have nitrogen attached to the phenyl group at a position which is meta relative to the boronate group.

21 Claims, 5 Drawing Sheets

(51) Int. Cl.
- C09K 8/90 (2006.01)
- C08L 5/00 (2006.01)
- C08L 101/02 (2006.01)
- C08J 3/24 (2006.01)
- C09K 8/12 (2006.01)
- C09K 8/512 (2006.01)
- C09K 8/575 (2006.01)
- C09K 8/68 (2006.01)
- C08B 37/00 (2006.01)
- A61K 8/73 (2006.01)
- A61Q 19/00 (2006.01)
- A61K 8/81 (2006.01)
- C11D 3/37 (2006.01)
- C11D 17/00 (2006.01)
- C09D 5/00 (2006.01)
- C08F 8/40 (2006.01)
- C08L 25/18 (2006.01)
- C09D 7/43 (2018.01)

(52) U.S. Cl.
CPC ............ *A61K 8/8164* (2013.01); *A61Q 19/00* (2013.01); *C08B 37/0096* (2013.01); *C08F 8/40* (2013.01); *C08J 3/246* (2013.01); *C08L 5/00* (2013.01); *C08L 25/18* (2013.01); *C08L 101/02* (2013.01); *C09D 5/00* (2013.01); *C09D 7/43* (2018.01); *C09K 8/12* (2013.01); *C09K 8/512* (2013.01); *C09K 8/5756* (2013.01); *C09K 8/685* (2013.01); *C09K 8/882* (2013.01); *C09K 8/885* (2013.01); *C09K 8/905* (2013.01); *C11D 3/3773* (2013.01); *C11D 17/003* (2013.01); *E21B 43/16* (2013.01); *A61K 2800/10* (2013.01); *A61K 2800/48* (2013.01); *A61K 2800/594* (2013.01); *A61K 2800/95* (2013.01); *C08J 2305/00* (2013.01); *C08J 2425/08* (2013.01)

(56) References Cited

U.S. PATENT DOCUMENTS

| | | |
|---|---|---|
| 2006/0058198 A1 | 3/2006 | Dessinges et al. |
| 2007/0281869 A1 | 12/2007 | Drochon et al. |
| 2008/0138386 A1 | 6/2008 | Joffre et al. |
| 2009/0163387 A1 | 6/2009 | Sullivan et al. |
| 2010/0179076 A1 | 7/2010 | Sullivan et al. |
| 2012/0103615 A1 | 5/2012 | Scherman et al. |
| 2013/0312970 A1 | 11/2013 | Lafitte et al. |

OTHER PUBLICATIONS

Yates et al., "Synthesis and applications of hyperbranched polymers," European Polymer Journal, 2004, vol. 40, Issue 7, pp. 1257-1281.

* cited by examiner

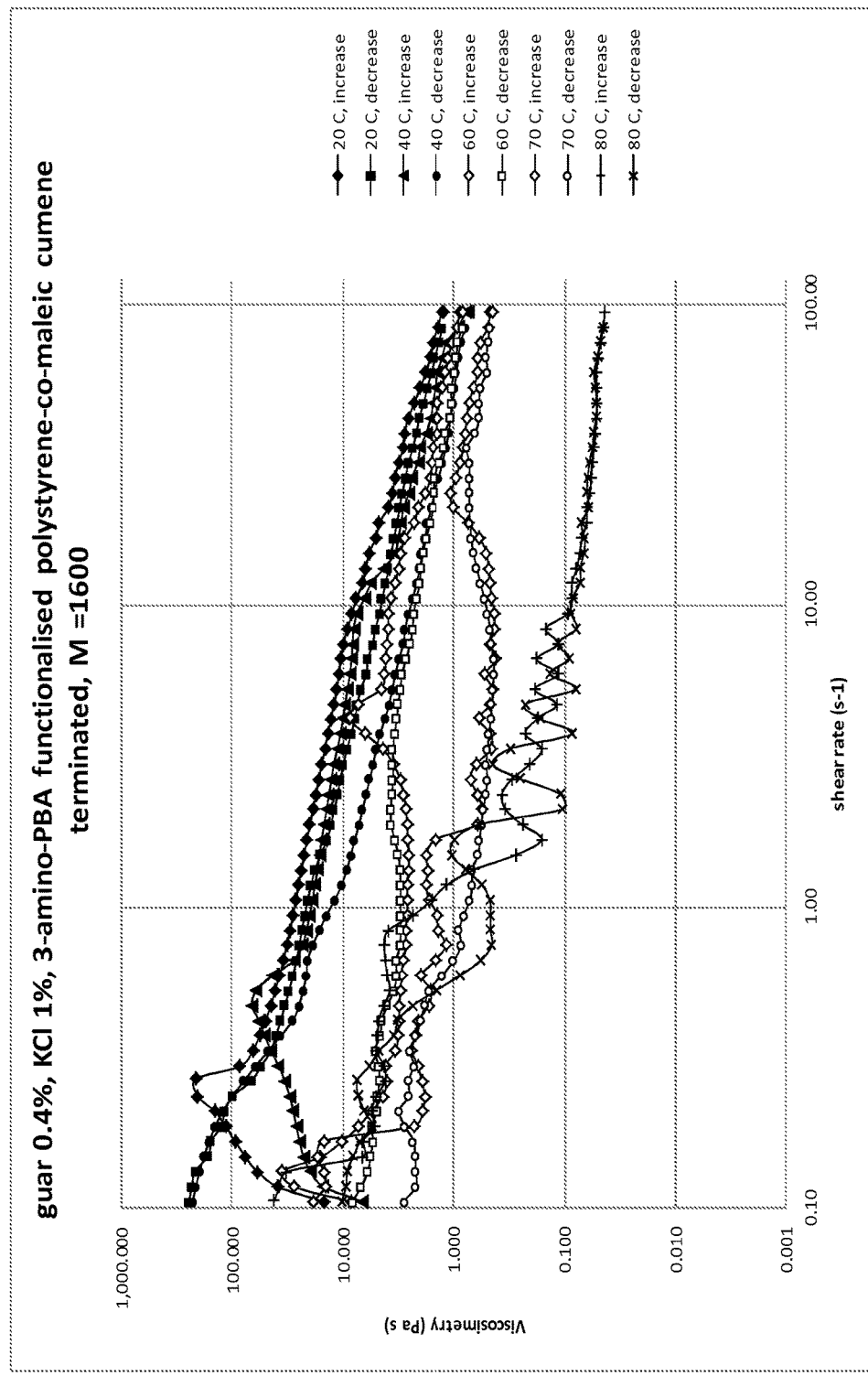

THICKENING OF FLUIDS

CROSS-REFERENCE TO RELATED APPLICATIONS

This application claims priority as a 35 USC 371 application to PCT application PCT/IB2013/053805 filed 10 May 2013 which claims priority from U.S. Provisional application 61/646,019 filed 11 May 2012. The disclosures of both applications above are incorporated by reference herein in their entireties.

BACKGROUND

It is well known to increase the viscosity of water or an aqueous solution by incorporating a polymer as a thickening agent. A number of polymers are known for this purpose including a number of polysaccharides. Viscosity can then be increased further by cross-linking the polymer molecules. This has particular application in connection with the extraction of hydrocarbons such as oil and natural gas from a reservoir which is a subterranean geologic formation by means of a drilled well that penetrates the hydrocarbon-bearing reservoir formation. In this field, one commercially very significant application of thickened fluids is for hydraulic fracturing of the formation. The polymeric thickening agent assists in controlling leak-off of the fluid into the formation, it aids in the transfer of hydraulic fracturing pressure to the rock surfaces and it facilitates the suspension and transfer into the formation of proppant materials that remain in the fracture and thereby hold the fracture open when the hydraulic pressure is released.

Further applications of thickened fluids in connection with hydrocarbon extraction are acidizing, control of fluid loss, diversion, zonal isolation, and the placing of gravel packs. Gravel packing is a process of placing a volume of particulate material, frequently a coarse sand, within the wellbore and possibly extending slightly into the surrounding formation. The particulate material used to form a gravel pack may be transported into place in suspension in a thickened fluid. When it is in place, the gravel pack acts as a filter for fine particles so that they are not entrained in the produced fluid.

Common examples of polymeric thickening agents used in the thickened fluids mentioned above are galactomannan gums, in particular guar and substituted guars such as hydroxypropyl guar. Cellulosic polymers such as hydroxyethyl cellulose may be employed, as well as other carbohydrate based polymers.

Crosslinking of the polymeric materials then serves to increase the viscosity and proppant carrying ability of the fluid, as well as to increase its high temperature stability. Typical crosslinking agents include soluble boron compounds.

The viscosity of these crosslinked gels can be reduced by mechanical shearing (ie they are shear thinning) but gels cross-linked with boron compounds have the advantage that they will reform spontaneously after exposure to high shear. This property of being reversible makes boron-crosslinked gels particularly attractive and they have been widely used.

It is generally desirable to achieve the desired viscosity with a low concentration of thickening materials so as to reduce cost of materials and reduce the amount of material which is delivered below ground and may need to be removed in a subsequent cleanup operation. It is also desirable to minimise the amount of boron which is used.

SUMMARY

This summary is provided to introduce a selection of concepts that are further described below. This summary is not intended to be used as an aid in limiting the scope of the subject matter claimed.

In a first aspect, an aqueous fluid comprises an aqueous solution or dispersion of a polymer and a cross linking agent to enhance the viscosity of the fluid by crosslinking the polymer, wherein the crosslinking agent is an organic polymer containing at least one polymer chain with boronate-containing groups distributed along the chain, wherein the boronate groups are phenyl boronate groups with a nitrogen atom attached to the phenyl group at a position meta to the boronate group.

In some embodiments, the fluid is a wellbore fluid intended for delivery via a wellbore to a subterranean location which may be a reservoir penetrated by the wellbore. It will be appreciated that until the crosslinking reaction occurs, the phenyl boronate groups may be present in boronic acid form, or partially or completely neutralized to boronate, depending on pH of the fluid. If the fluid is alkaline, the cross linking reaction may be reaction with phenyl borate groups on the crosslinking agent.

In a second aspect, a method of treatment of a wellbore or a formation penetrated by a wellbore, comprises pumping into the wellbore a fluid comprising an aqueous solution or dispersion of a polymer and also a cross linking agent to enhance the viscosity of the fluid by crosslinking the polymer, wherein the crosslinking agent is an organic polymer containing at least one polymer chain with boronate-containing groups distributed along the chain, wherein the boronate groups are phenyl boronate groups with a nitrogen atom attached to the phenyl group at a position meta to the boronate group.

The phenyl boronate groups may be attached to the polymer chain through such a nitrogen atom. In this case the phenyl boronate groups may have formula

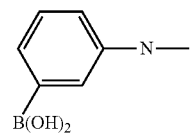

and the nitrogen atom may be part of an amine or an amide group.

It is also possible that the nitrogen atom is part of a substituent group, such as a nitro group meta to the boronate group. In such a case the phenyl boronate groups may have formulae

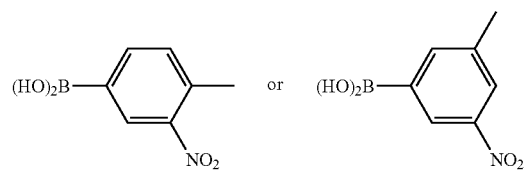

The crosslinking polymer to which the phenyl boronate groups are attached may be a linear polymer with a single polymer chain or may be a branched polymer with multiple chains. Phenyl boronate groups may be attached directly to or close to the backbone of a polymer chain or may be attached to pendant side chains.

Although the purpose of this polymer is to act as a crosslinking agent, it may itself incorporate cross links, for instance cross links connecting linear chains bearing phenyl boronate groups.

This polymer bearing phenyl boronate groups may have a wide range of compositions. It may be made using a co-monomer which includes phenyl boronate groups, or it may be made by modifying a polymer to incorporate phenyl boronate groups.

The first mentioned polymer which is to be crosslinked may be a polysaccharide or chemically modified polysaccharide. The amount of this polymer may be no more than 1% by weight of the fluid, possibly no more than 0.5%. The amount may be at least 0.05% such as in a range from 0.05 to 0.25% by weight of the fluid.

The concentration of boron in the fluid may lie in a range from 5 to 50 ppm elemental boron and possibly no more than 25 ppm. The quantity of the cross linking agent (polymer including phenyl boronate groups) may be no more than 30%, possibly no more than 20, 15 or 10% by weight of the polymer to be crosslinked.

We have observed that these polymers can cross link polymer to a higher viscosity than inorganic boron used at the same boron concentration. We have also observed that satisfactory cross-linking can occur when the polymer which is to be cross-linked is at a lower concentration than is usually required. Thus the boron concentration may be lower than usual and/or the concentration of the polymer which is cross linked may be lower than usual. Concentration of polysaccharide or chemically modified polysaccharide in the fluid may be from 0.5 or 1 g/liter up to 5 g/liter or even more such as 10 or 20 g/liter, but quite possibly not over 2 g/liter.

In some embodiments of the invention, the crosslinking agent contains material which serves an additional purpose (something other than binding to polymer molecules) so that the crosslinking agent is multifunctional. For instance the crosslinking agent may incorporate a detectable tracer material. This could be used to monitor the presence/amount of cross-linked polymer in fluid flowing out of a well, for instance during flow back after hydraulic fracturing. Such a tracer could be a coloured material such as a dye or a fluorescent material and the presence of the tracer could be determined by spectroscopy. Another possibility is that a tracer could be provided by a redox active material, such as ferrocene or a ferrocene derivative, detectable by electrochemistry. In either case the tracer material could be incorporated into nanoparticles during their preparation, for example by incorporating a comonomer with the tracer covalently attached to it. However, we have observed that hydrophobic tracer can be absorbed into nanoparticles with a hydrophobic core and it is then retained well by the nanoparticles, thus providing the particles with a detectable tracer material in them. Further possibilities are that the crosslinking agents may incorporate or be attached to corrosion inhibitors or chelating agents for scale-forming ions.

Although wellbore fluids for delivery to a subterranean location have been discussed above, other applications of this invention are products where a thickened fluid is required. Many detergent compositions and cosmetic compositions are thickened fluids. For instance household cleaning compositions including hard surface compositions containing suspended solid, personal washing compositions such as shower gels, shampoos and conditioners, roll-on deodorants and others. Another area where thickened aqueous liquids are employed are water-based paints containing pigment.

A wellbore fluid embodying the present invention may include other constituents in addition to those already mentioned. One additional constituent which may be included is a breaker. The purpose of this component is to "break" or diminish the viscosity of the fluid so that this fluid is more easily recovered from the formation during cleanup. The breaker degrades the polymer to reduce its molecular weight. If the polymer is a polysaccharide, the breaker may be a peroxide with oxygen-oxygen single bonds in the molecular structure. These peroxide breakers may be hydrogen peroxide or other material such as a metal peroxide that provides peroxide or hydrogen peroxide for reaction in solution. A peroxide breaker may be a so-called stabilized peroxide breaker in which hydrogen peroxide is bound or inhibited by another compound or molecule(s) prior to its addition to water but is released into solution when added to water.

Examples of suitable stabilized peroxide breakers include the adducts of hydrogen peroxide with other molecules, and may include carbamide peroxide or urea peroxide ($CH_4N_2O.H_2O_2$), percarbonates, such as sodium percarbonate ($2Na_2CO3.3H_2O_2$), potassium percarbonate and ammonium percarbonate. The stabilized peroxide breakers may also include those compounds that undergo hydrolysis in water to release hydrogen peroxide, such sodium perborate. A stabilized peroxide breaker may be an encapsulated peroxide. The encapsulation material may be a polymer that can degrade over a period of time to release the breaker and may be chosen depending on the release rate desired. Degradation of the polymer can occur, for example, by hydrolysis, solvolysis, melting, or other mechanisms. The polymers may be selected from homopolymers and copolymers of glycolate and lactate, polycarbonates, polyanhydrides, polyorthoesters, and polyphosphacenes. The encapsulated peroxides may be encapsulated hydrogen peroxide, encapsulated metal peroxides, such as sodium peroxide, calcium peroxide, zinc peroxide, etc. or any of the peroxides described herein that are encapsulated in an appropriate material to inhibit or reduce reaction of the peroxide prior to its addition to water.

The peroxide breaker, stabilized or unstabilized, is used in an amount sufficient to break the heteropolysaccharide polymer or diutan. This may depend upon the amount of heteropolysaccharide used and the conditions of the treatment. Lower temperatures may require greater amounts of the breaker. In many, if not most applications, the peroxide breaker may be used in an amount of from about 0.001% to about 20% by weight of the treatment fluid, more particularly from about 0.005% to about 5% by weight of the treatment fluid, and more particularly from about 0.01% to about 2% by weight of the treatment fluid. The peroxide breaker may be effective in the presence of mineral oil or other hydrocarbon carrier fluids or other commonly used chemicals when such fluids are used with the heteropolysaccharide.

Breaking aids or catalysts may be used with the peroxide breaker. The breaker aid may be an iron-containing breaking aid that acts as a catalyst. The iron catalyst is a ferrous iron (II) compound. Examples of suitable iron (II) compounds include, but are not limited to, iron (II) sulfate and its hydrates (e.g ferrous sulfate heptahydrate), iron (II) chloride, and iron (II) gluconate. Iron powder in combination with a pH adjusting agent that provides an acidic pH may also be used. Other transition metal ions can also be used as the breaking aid or catalyst, such as manganese (Mn).

Other materials which may included in a wellbore fluid include electrolyte, such as an organic or inorganic salt, friction reducers to assist flow when pumping and surfactants.

A wellbore fluid may be a so-called energized fluid formed by injecting gas (most commonly nitrogen, carbon dioxide or mixture of them) into the wellbore concomitantly with the aqueous solution. Dispersion of the gas into the base fluid in the form of bubbles increases the viscosity of such fluid and impacts positively its performance, particularly its ability to effectively induce hydraulic fracturing of the formation, and capacity to carry solids. The presence of the gas also enhances the flowback of the fluid when this is required. In a method of this invention the wellbore fluid may serve as a fracturing fluid or gravel packing fluid and may be used to suspend a particulate material for transport down wellbore. This material may in particular be a proppant used in hydraulic fracturing or gravel used to form a gravel pack. The commonest materials used as proppant or gravel is sand of selected size but ceramic particles and a number of other materials are known for this purpose.

Wellbore fluids in accordance with this invention may also be used without suspended proppant in the initial stage of hydraulic fracturing. Further applications of wellbore fluids in accordance with this invention are in modifying the permeability of subterranean formations, and the placing of plugs to achieve zonal isolation and/or prevent fluid loss.

For some applications a fiber component may be included in the treatment fluid to achieve a variety of properties including improving particle suspension, and particle transport capabilities, and gas phase stability. Fibers used may be hydrophilic or hydrophobic in nature. Fibers can be any fibrous material, such as, but not necessarily limited to, natural organic fibers, comminuted plant materials, synthetic polymer fibers (by non-limiting example polyester, polyaramide, polyamide, novoloid or a novoloid-type polymer), fibrillated synthetic organic fibers, ceramic fibers, inorganic fibers, metal fibers, metal filaments, carbon fibers, glass fibers, ceramic fibers, natural polymer fibers, and any mixtures thereof. Particularly useful fibers are polyester fibers coated to be highly hydrophilic, such as, but not limited to, DACRON® polyethylene terephthalate (PET) fibers available from Invista Corp., Wichita, Kans., USA, 67220. Other examples of useful fibers include, but are not limited to, polylactic acid polyester fibers, polyglycolic acid polyester fibers, polyvinyl alcohol fibers, and the like. When used in fluids of the invention, the fiber component may be present at concentrations from about 1 to about 15 grams per liter of the liquid phase, in particular the concentration of fibers may be from about 2 to about 12 grams per liter of liquid, and more particularly from about 2 to about 10 grams per liter of liquid.

BRIEF DESCRIPTION OF THE DRAWINGS

FIG. 6 is a graph of viscosity of guar in a salt solution.

EXAMPLE 1

Figure 1:
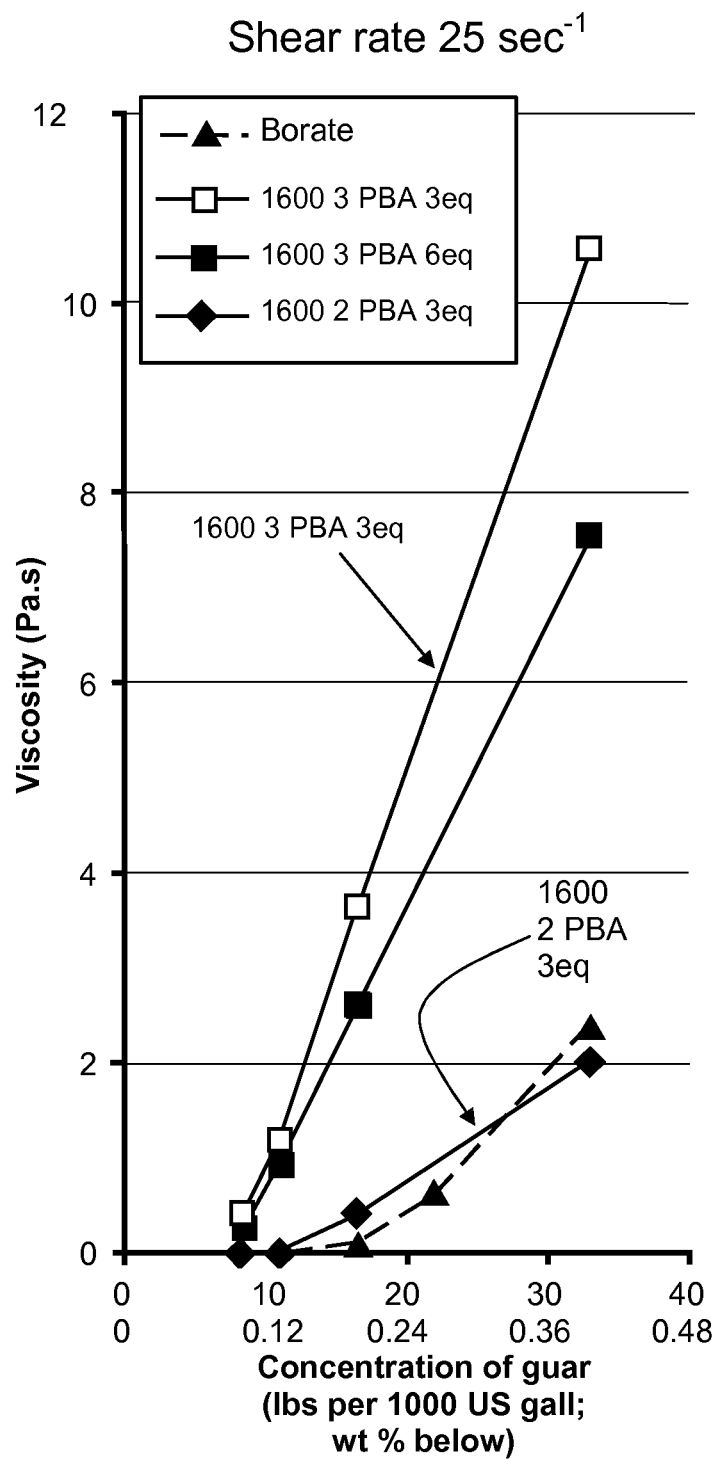
FIGS. 1 and 2 are graphs of viscosity of thickened guar at ambient temperature.

A number of crosslinking agents were made, starting from copolymers of styrene and maleic anhydride. This polystyrene-co-maleic anhydride copolymer has high water solubility and is known to react with nucleophiles such as hydroxyl or amines. The copolymer was reacted with an aminophenylboronic acid in anhydrous tetrahydrofuran (THF) under reflux conditions. In a second step, the crude polymer was redissolved in water/NaOH which opened any remaining maleic anhydride rings. This two step reaction is illustrated thus:

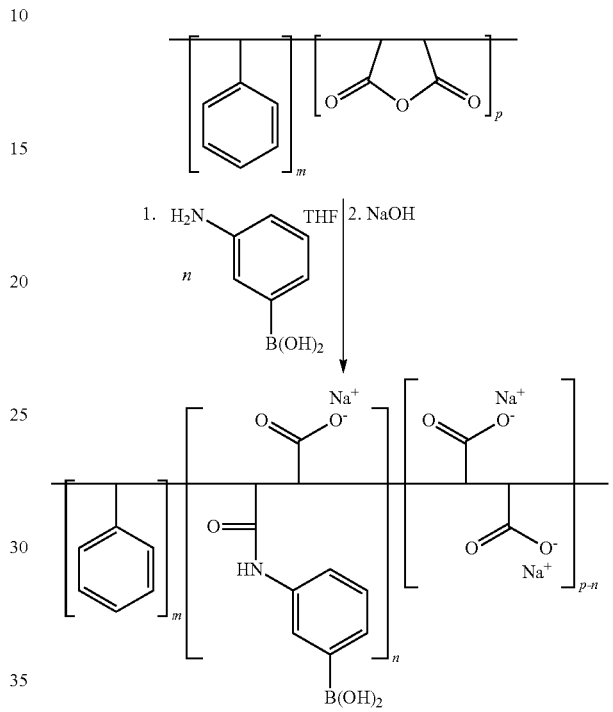

Commercially available polystyrene-co-maleic anhydrides with varying molecular weight and ratio of styrene/maleic units were used.

Synthesis of Functionalised Polystyrene-Co-Maleic Anhydride 2 g of polystyrene-co-maleic anhydride terminated with cumene and having Mn=1600 (1.25×10−3 mol, 5.8 maleic moieties per chain) and a chosen amount of 3-amino phenyl boronic acid were added to 80 ml of tetrahydrofuran. The solution was stirred at 60° C. for 24 h. The solvent was evaporated with a rotary evaporator and the solid was redissolved in water made alkaline to pH=11. Excess water was evaporated and the product polymer was freeze-dried for 48 h.

This procedure was carried out using amino phenyl boronic acids as follows

| Acid | | | Equivalents per polymer chain |
|---|---|---|---|
| 3-amino phenyl boronic acid monohydrate | 621 mg | $4.00 \times 10^{-3}$ mol | 3 |
| 3-amino phenyl boronic acid monohydrate | 1242 mg | $8.00 \times 10^{-3}$ mol | 6 |
| 2-amino phenyl boronic acid | 1096 mg | $8.00 \times 10^{-3}$ mol | 6 |
| 4-aminophenyl boronic acid hydrochloride | 1387 mg | $8.00 \times 10^{-3}$ mol | 6 |

This procedure was also carried out using 1 g of polystyrene-co-maleic anhydride Mn=5000 ($2.0 \times 10^{-4}$ mol, 20 maleic moieties per chain) and 630 mg of 3-aminophenylboronic acid monohydrate.

The same procedure was repeated using 2 g of polystyrene-co-maleic anhydride Mn=9500 ($2.1 \times 10^{-4}$ mol) and amounts of amino phenyl boronic acid as in the following table

| Acid | | | Equivalents per polymer chain |
|---|---|---|---|
| 3-amino phenyl boronic acid monohydrate | 315 mg | $2.04 \times 10^{-3}$ mol | 10 |
| 3-amino phenyl boronic acid monohydrate | 630 mg | $4.08 \times 10^{-3}$ mol | 19 |

For all of the polymers synthesized as above, the amount of boron within the polymer was measured by ICP-MS. Using solutions made with 150 mg of polymer in 2.50 ml of water and diluted 2000 times with 1% nitric acid. Calibration curves were obtained from boron standard solution (1000 ppmB). The results were

| Polymer | Abbreviation | Ratio of boron to polymer |
|---|---|---|
| Ps-co-Ma 1600 3PBA 3eq | Poly1600-3-3 | $13.0 \pm 1.3$ mg/g |
| Ps-co-Ma 1600 3PBA 6eq | Poly 1600-3-6 | $24.5 \pm 1.2$ mg/g |
| Ps-co Ma 5000 3PBA 18eq | Poly 5000-3-18 | $21.0 \pm 2.1$ mg/g |
| Ps-co-Ma 9500 3PBA 10eq | Poly9500-3-10 | $8.1 \pm 0.8$ mg/g |
| Ps-co-Ma 9500 3PBA 20eq | Poly 9500-3-20 | $10.1 \pm 1.2$ mg/g |
| Ps-co Ma 1600 2PBA 6eq | Poly 1600-2-6 | $22.3 \pm 2.2$ mg/g |
| Ps-co-Ma 1600 4PBA 6eq | Poly 1600-4-6 | $10.5 \pm 1.0$ mg/g |

Testing Under Standard Conditions

Crosslinking agents prepared as above were tested for ability to crosslink unmodified guar. An aqueous guar solution containing guar at a concentration of 4 gm/liter, equivalent to 33 lbs per 1000 US gallons was first prepared by mixing guar powder with de-ionised water in a Waring blender for 30 minutes. Polymer, prepared as above, was added to a 15 ml aliquot of the guar solution in an amount to give a boron concentration of 60 ppm. As a comparison, inorganic borate was added to a quantity of the same guar solution so as to give a boron concentration of 60 ppm. Portions of each mixture were diluted so as to provide lower concentrations of guar and boron, with the same guar to boron ratio. The lowest guar concentration was 1 gm/liter containing 0.75 ppm boron as polymer or 15 ppm boron as borate.

After mixing, the pH was raised above 9.5 to allow crosslinking and thickening to occur, and after a delay of 7 minutes, viscosities were measured at 25° C. at shear rates of 25 $sec^{-1}$.

Figure 2:
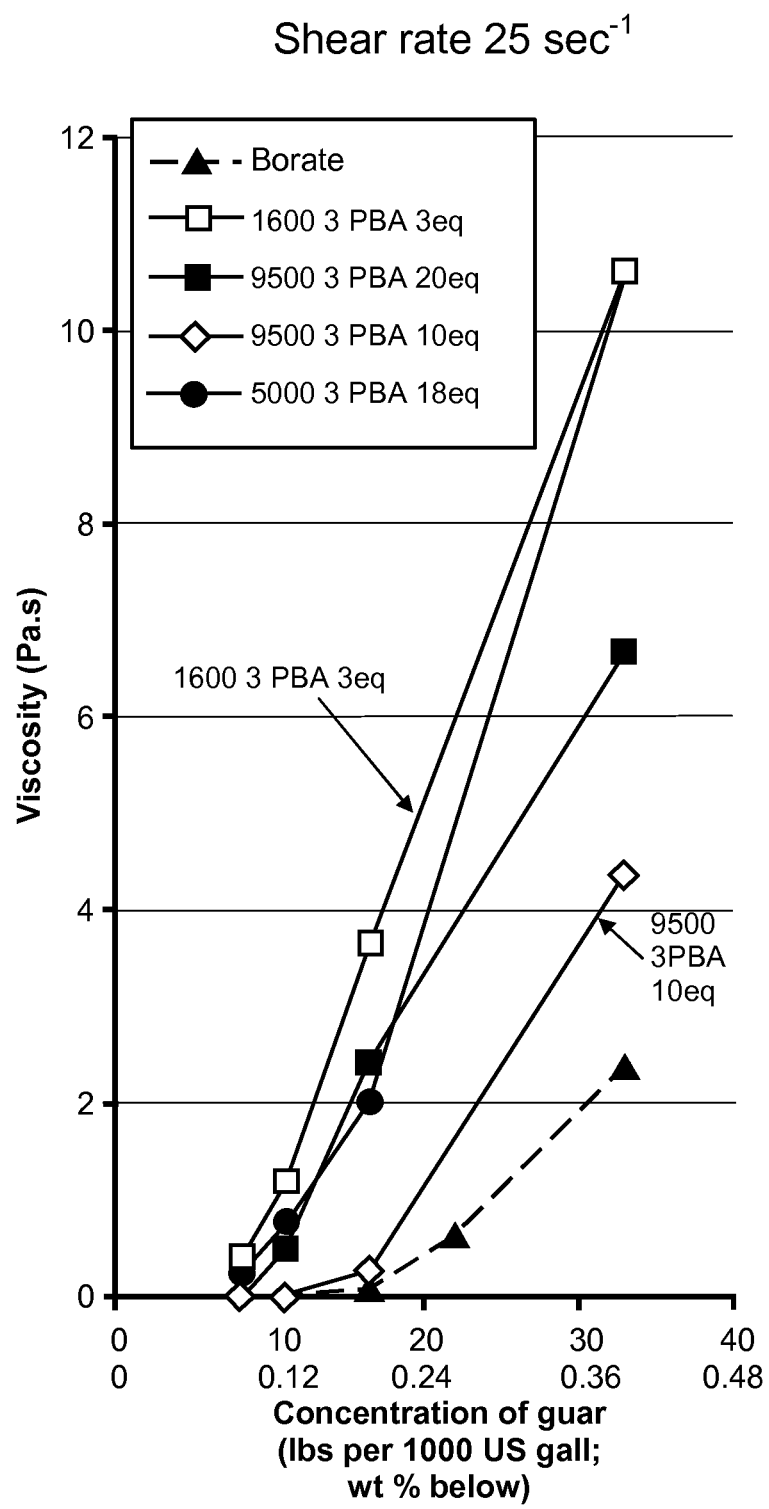

It was found that poly 1600-4-6 failed to cross link guar. Other results are shown in FIG. 1 and FIG. 2 where solid lines show data for crosslinking polymers and broken lines show the data points for inorganic borate.

It can be seen from these graphs that the cross linking polymers made using 3-amino phenyl boronic acid achieved much higher viscosities than inorganic borate with the same concentrations of boron and guar, and were able to achieve similar viscosities to borate even when the amount of guar and boron was reduced to half.

Testing Under Temperature

Figure 3:
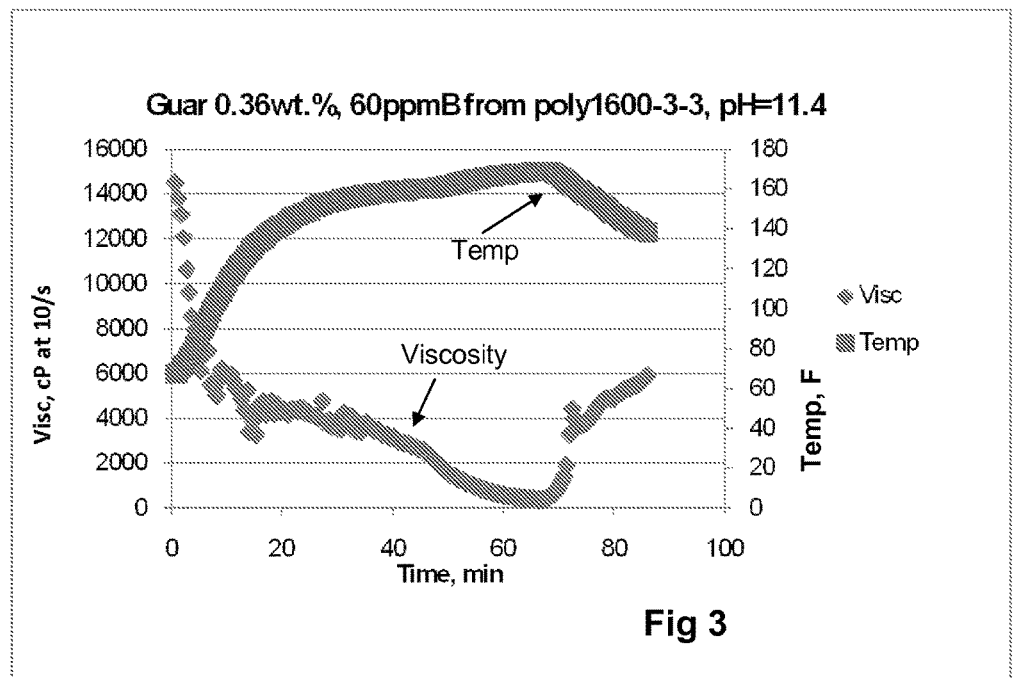
FIGS. 3, 4 and 5 show viscosity of thickened guar as temperature is raised and lowered.
Figure 4:
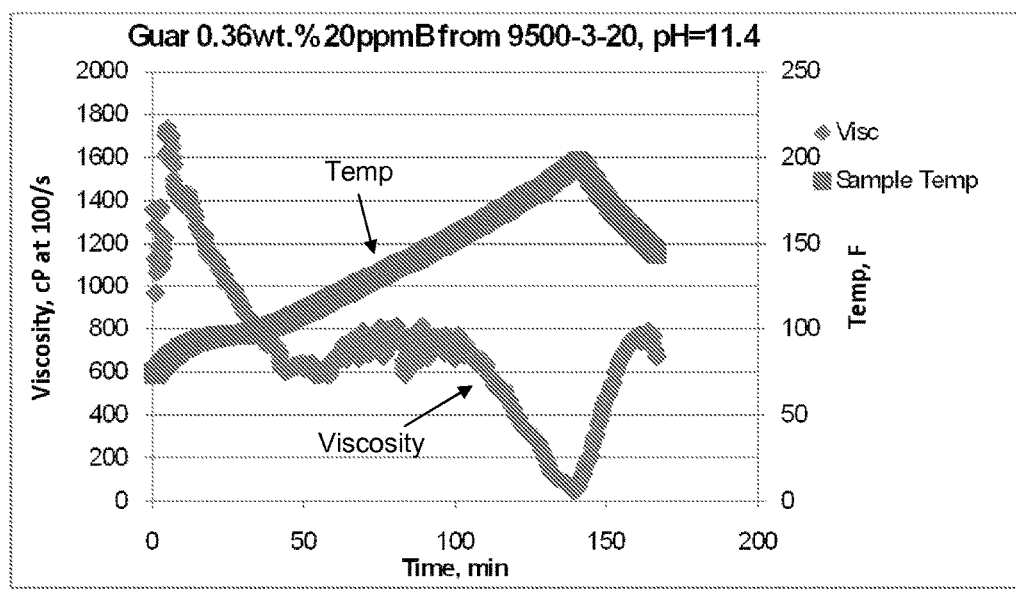

An aqueous guar solutions containing guar at a concentration of 0.36 gm/liter, equivalent to 30 lbs per 1000 US gallons was thickened with poly 1600-3-3 in an amount to provide 60 ppm boron in solution. A similar solution was thickened with poly 9500-3-20 in an amount to provide 20 ppm boron in solution. After mixing, pH was raised to 11.4 to thicken the solutions. Viscosity was monitored as temperature was progressively increased and then reduced again, so as to find the melting temperature of the crosslinked gels. Results are shown in FIGS. 3 and 4.

The solution of guar thickened with poly 1600-3-3 progressively lost viscosity at temperatures above about 150° F. and had little or no viscosity above 160° F. However, its viscosity recovered somewhat when temperature was reduced. The sample thickened with the higher molecular weight poly 9500-3-20 showed better stability of viscosity in the temperature range 100-150° F., lost viscosity when temperature was raised to 200° F. and also recovered viscosity on cooling.

Testing in a Salt Solution.

An aqueous guar solution containing guar at a concentration of 0.4 gm/liter (0.4 wt %) was made as above while also including 1 wt % potassium chloride. A portion of the solution was successfully thickened with poly 1600-3-3 in an amount to provide 60 ppm boron in solution. An attempt was also made to thicken another portion with poly 1600-2-3 (made as above from 2-amino phenyl boronic acid) but the viscosity at low shear was about 1000 times lower. Such a solution cannot be thickened with inorganic borate: precipitation occurs.

Viscosity of the solution thickened with poly 1600-3-3 was measured at a range of shear rates at 20° C., then the solution was heated in stages to 80° C. and cooled in stages back to 20° C., with viscosity measured over the range of shear rates at each temperature step. These viscosity measurements are shown as FIG. 6.

EXAMPLE 2

A cross linking polymer was made by reacting polybenzyl chloride with 3 amino phenyl boronic acid in tetrahydrofuran, thus.

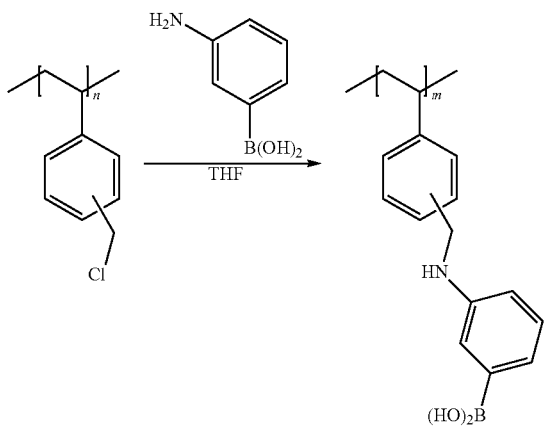

The polybenzylchoride had a molecular weight of about 100,000 which corresponds to about 660 benzyl chloride groups in a polymer chain. The amount of 3-phenyl boronic acid was chosen to introduce about 500 phenyl boronate groups per polymer chain.

Figure 5:
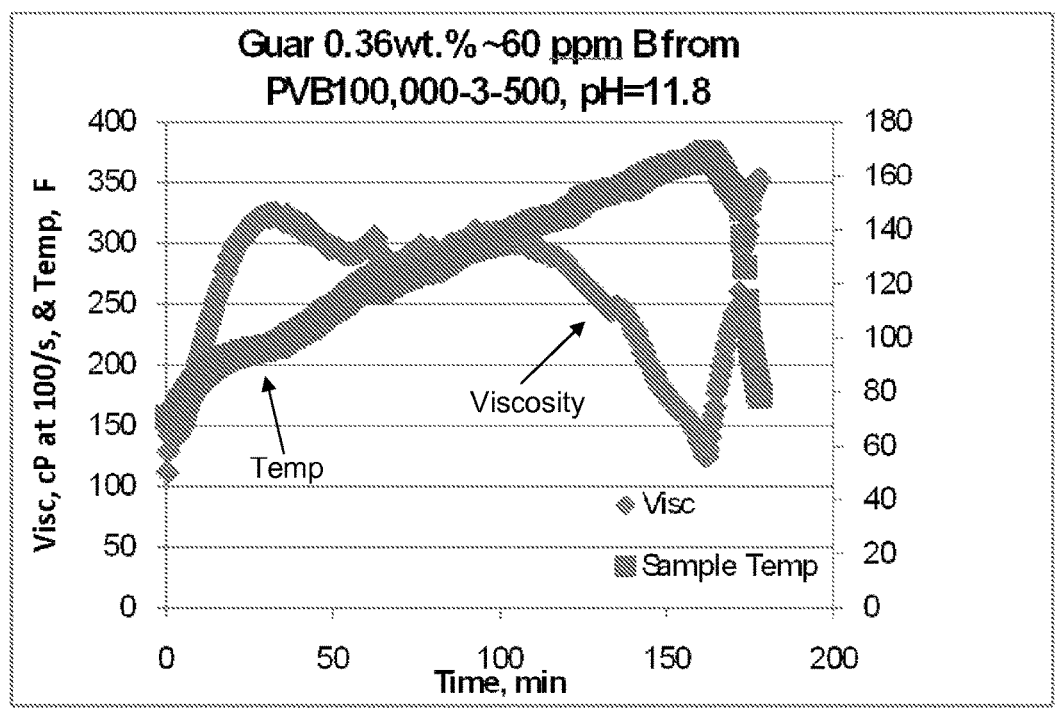

A solution containing guar at a concentration of 0.36 gm/liter, equivalent to 30 lbs per 1000 US gallons was thickened with this cross linking polymer in an amount to provide 60 ppm boron in solution. The thickened solution was tested as in the previous example by monitoring viscosity as temperature was progressively increased and then reduced again. The results are shown as FIG. 5. It can be seen that substantial viscosity was maintained up to about 140° F. The viscosity reduced at higher temperatures but recovered when temperature was reduced.

It will be appreciated that example embodiments such as described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

The invention claimed is:

1. A wellbore treatment fluid comprising:
an aqueous solution or dispersion of a first polymer to thicken the fluid;
a cross-linking agent to increase viscosity of the fluid by cross-linking the first polymer, wherein the cross-linking agent is a second polymer comprising at least one polymer chain with phenyl boronate groups distributed along the polymer chain, and wherein each phenyl boronate group comprises a phenyl group and a boronate group and has a nitrogen atom attached to the phenyl group at a position which is meta relative to the boronate group; and
a viscosity breaker to reduce viscosity of the fluid after a period of time.

2. The wellbore treatment fluid of claim 1, wherein each phenyl boronate group is attached to the polymer chain through the nitrogen atom.

3. The wellbore treatment fluid of claim 1, wherein the phenyl boronate groups have a nitro substituent on the phenyl group at a position meta to the boronate group.

4. The wellbore treatment fluid of claim 1, wherein the concentration of the first polymer is in a range from 0.5 to 5 g/liter.

5. The wellbore treatment fluid of claim 1, wherein the concentration of the first polymer is no more than 2 g/liter.

6. The wellbore treatment fluid of claim 1, wherein the first polymer is a polysaccharide or a chemically modified polysaccharide.

7. The wellbore treatment fluid of claim 1, wherein the content of boron in the fluid is between about 5 and about 25 ppm by weight elemental boron.

8. The wellbore treatment fluid of claim 1, wherein the cross-linking agent includes a colored or fluorescent material to act as a tracer.

9. A method of treatment of a wellbore or a formation penetrated by a wellbore, the method comprising:
pumping into the wellbore a fluid comprising:
an aqueous solution or dispersion of a first polymer; and
a cross-linking agent to increase viscosity of the fluid by cross-linking the first polymer, wherein the cross-linking agent is a second polymer comprising at least one polymer chain with phenyl boronate groups distributed along the polymer chain, and wherein each phenyl boronate group comprises a phenyl group and a boronate group and has a nitrogen atom attached to the phenyl group at a position which is meta relative to the boronate group.

10. The method of claim 9, wherein the phenyl boronate groups are attached to the polymer chain through the said-nitrogen atom.

11. The method of claim 9, wherein the phenyl boronate groups have a nitro substituent on the phenyl ring at a position meta to the boronate group.

12. The method of claim 9, wherein a concentration of the first polymer in the fluid is in a range from about 0.5 to about 2 g/liter.

13. The method of claim 9, wherein the first polymer is a polysaccharide or a chemically modified polysaccharide.

14. The method of claim 9, wherein a content of boron in the fluid is between about 5 and about 25 ppm by weight elemental boron.

15. The method of claim 9, wherein the cross-linking agent includes a colored or fluorescent material to act as a tracer.

16. The wellbore treatment fluid of claim 1, wherein the fluid is a fracturing fluid and contains suspended proppant.

17. A wellbore treatment fluid comprising:
an aqueous solution or dispersion of a first polymer to thicken the fluid; and
a cross-linking agent to increase viscosity of the fluid by cross-linking the first polymer, wherein the cross-linking agent is a second polymer comprising at least one polymer chain with phenyl boronate groups distributed along the polymer chain, and wherein each phenyl boronate group comprises a phenyl group and a boronate group and has a nitrogen atom attached to the phenyl group at a position which is meta relative to the boronate group;
wherein the wellbore treatment fluid is a gravel packing fluid and contains gravel.

18. A wellbore treatment fluid comprising:
an aqueous solution or dispersion of a first polymer to thicken the fluid;
a cross-linking agent to increase viscosity of the fluid by cross-linking the first polymer, wherein the cross-linking agent is a second polymer comprising at least one polymer chain with phenyl boronate groups distributed along the polymer chain, and wherein each phenyl boronate group comprises a phenyl group and a boronate group and has a nitrogen atom attached to the phenyl group at a position which is meta relative to the boronate group; and
one or more of a corrosion inhibitor, a chelating agent, an electrolyte, or a friction reducer.

19. A wellbore treatment fluid comprising:
an aqueous solution or dispersion of a first polymer to thicken the fluid; and
a cross-linking agent to increase viscosity of the fluid by cross-linking the first polymer, wherein the cross-linking agent is a second polymer comprising at least one polymer chain with phenyl boronate groups distributed along the polymer chain, and wherein each phenyl boronate group comprises a phenyl group and a boronate group and has a nitrogen atom attached to the phenyl group at a position which is meta relative to the boronate group;
wherein the wellbore treatment fluid is an energized fluid formed by injecting gas into a wellbore concomitantly with the wellbore treatment fluid.

20. A wellbore treatment fluid comprising:
an aqueous solution or dispersion of a first polymer to thicken the fluid; and
a cross-linking agent to increase viscosity of the fluid by cross-linking the first polymer, wherein the cross-linking agent is a second polymer comprising at least one polymer chain with phenyl boronate groups distributed along the polymer chain, and wherein each phenyl boronate group comprises a phenyl group and a boronate group and has a nitrogen atom attached to the phenyl group at a position which is meta relative to the boronate group;

wherein the wellbore treatment fluid contains plugs to achieve zonal isolation or to prevent fluid loss.

21. A wellbore treatment fluid comprising:

an aqueous solution or dispersion of a first polymer to thicken the fluid;

a cross-linking agent to increase viscosity of the fluid by cross-linking the first polymer, wherein the cross-linking agent is a second polymer comprising at least one polymer chain with phenyl boronate groups distributed along the polymer chain, and wherein each phenyl boronate group comprises a phenyl group and a boronate group and has a nitrogen atom attached to the phenyl group at a position which is meta relative to the boronate group; and a fiber component to improve one or more of particle suspension, particle transport capabilities, or gas phase stability.

* * * * *